United States Patent [19]
Chung

[11] Patent Number: 5,429,622
[45] Date of Patent: Jul. 4, 1995

[54] HYGIENIC CLOTH FOR MALE BABY

[76] Inventor: Seon Y. Chung, Kocheung Jukong Apt. 1313-201, Haan-Dong, Kwanmyung, Kyeongki, Rep. of Korea

[21] Appl. No.: 227,091

[22] Filed: Apr. 13, 1994

Related U.S. Application Data

[63] Continuation of Ser. No. 867,094, Jun. 25, 1992, abandoned.

[30] Foreign Application Priority Data

Nov. 29, 1990 [KR] Rep. of Korea ............. 1990-16419

[51] Int. Cl.[6] ............................................. A61F 13/15
[52] U.S. Cl. ................................. 604/312; 604/347; 604/385.1; 604/386; 604/402
[58] Field of Search ......................... 604/304–307, 604/312, 317, 327, 346–358, 385.1–386, 393–398; 128/849–856, 883, 888, 889, 891, 402; 602/60, 67–73; 206/438–441, 65.3

[56] References Cited

U.S. PATENT DOCUMENTS

| 1,052,765 | 2/1913 | Strauss | 602/67 |
| 1,992,351 | 2/1935 | Burnell | 602/67 |
| 2,294,066 | 8/1942 | Baehler | 602/70 |
| 2,888,014 | 5/1959 | Dougherty | 607/70 |
| 4,195,630 | 4/1980 | Connery et al. | 602/67 |
| 4,244,367 | 1/1981 | Rollonhagon | 604/396 |
| 4,690,681 | 9/1987 | Haunsschild et al. | 604/396 |
| 4,702,239 | 10/1987 | Ichikawa | 602/67 |
| 4,731,065 | 3/1988 | Yamada | 664/355 |

FOREIGN PATENT DOCUMENTS

| 0575307 | 7/1924 | France | 604/349 |
| 2042342 | 9/1980 | United Kingdom | 604/349 |

Primary Examiner—Randall L. Green
Assistant Examiner—K. M. Reichle
Attorney, Agent, or Firm—Notaro & Michalos

[57] ABSTRACT

A hygienic device for the genitalia of a male infant comprises a cloth having a U-shaped separator. The separator and the cloth define a first hole which is large enough to accommodate the scrotum and the penis of the male infant. The separator has a second hole which is smaller than the first hole for accommodating the penis.

1 Claim, 1 Drawing Sheet

HYGIENIC CLOTH FOR MALE BABY

This application is a continuation of application Ser. No. 07/867,094, filed Jun. 25, 1992 now abandoned, which is a 371 of PCT/KR91/00027, filed Oct. 28, 1991.

FIELD AND BACKGROUND OF THE INVENTION

The present invention relates to a hygienic cloth for a male baby.

A baby who wears diapers is used to being wet around the groin area. It has been recognized that bacteria are produced by the secretions of sweat and the like which are excreted from parts of the human body which are in contact with other parts of the human body. The secretions cause many kinds of skin diseases and can be unpleasant to a baby because its skin is very soft. Also, the groin area is always wet due to the secretion of sweat even though the baby doesn't urinate.

SUMMARY OF THE INVENTION

The present invention is designed to protect a baby from many kinds of skin disease and to make the baby pleasant and comfortable by maintaining the skin dry while the baby doesn't urinate.

The present invention is a hygienic cloth worn under a diaper for a male baby, and comprises a hole in a soft absorbent cloth in order to separate the testicles from the groin area by allowing the testicles and the penis to extend out of the hole. Therefore, it is necessary to have a hole in the soft absorbent cloth, and the size of the hole should be large enough in order to accommodate the testicles and the penis. Moreover, the present invention is designed to isolate the penis from a testicles by the separator which comprises a loop on the upper part of the hole, which allows one to isolate the penis from the testicles by inserting the penis into the loop. However, a loop on the soft cloth which is separate, would prove to be expensive and require more resources to produce. Therefore, the present invention is designed to isolate the testicles and the penis by inserting a penis into the small hole at the middle of a flap or a loop which is produced due to having a substantial hole as a separator.

The present invention will become more fully understood from the detailed description given herein below and the accompanying drawings.

DESCRIPTION OF THE PREFERRED EMBODIMENT

Figure 1:
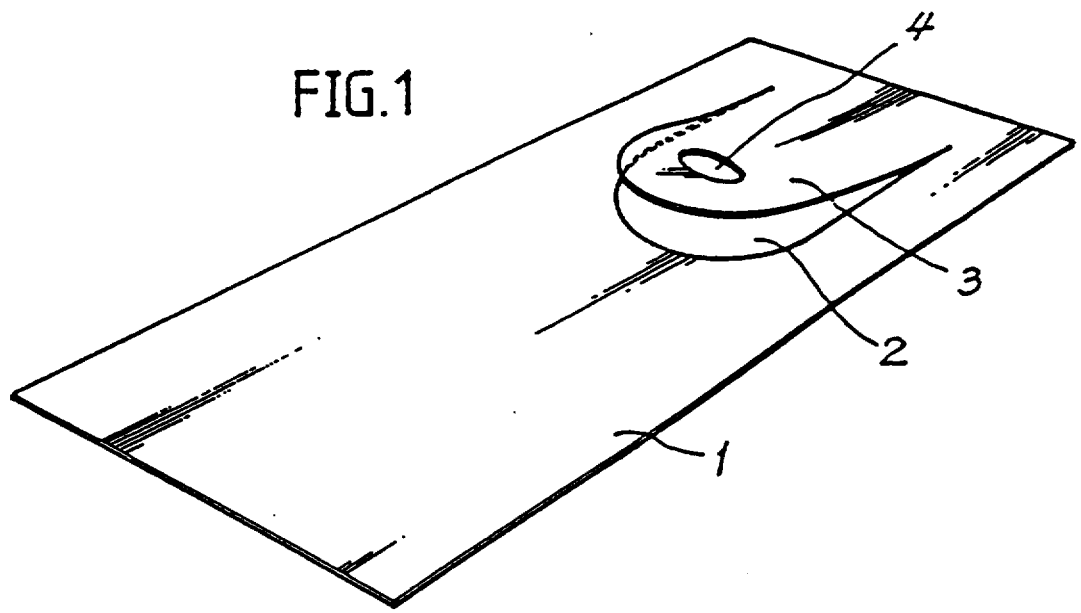
FIG. 1 is a perspective view of the present invention.

As shown in FIG. 1 the present invention comprises a main cloth (1) having a first hole (2) provided on the main cloth (1). The cloth (1) is made of an absorbing material which is soft. The size of the first hole (2) is large enough in size to accommodate the testicles and the penis of a male infant by allowing them to be inserted through the first hole (2). The first hole (2) is made through the main cloth (1) by cutting a line in the shape of an "U" as shown in FIG. 1, and this U-shaped portion forms a separator (3) made in the main cloth (1). The separator (3) can be made in the course of the making the first hole (2). A second hole (4), which is smaller than first hole (2), is made through the separator (3). The size of the second hole (4) should be made large enough to accommodate the penis. The structure denoted by reference numeral 5 is a diaper as shown in FIG. 2.

Figure 2:
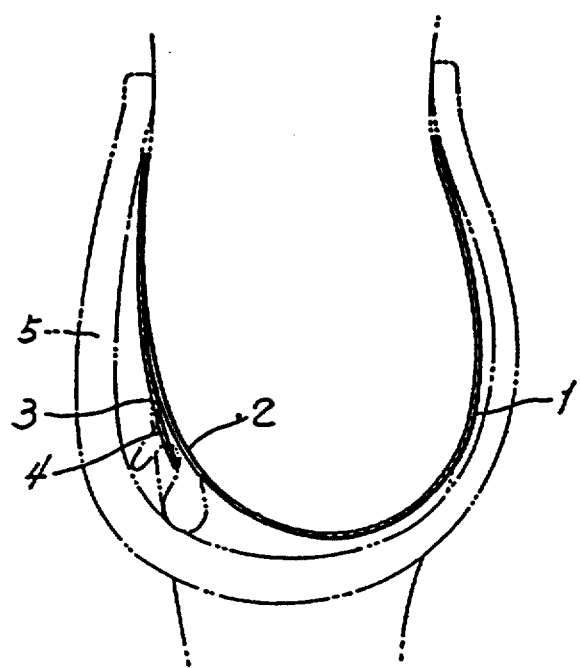
FIG. 2 is a vertical cross-sectional view of the present invention in combination with a diaper on a user.

Thus, as shown in FIG. 2, the present invention isolates the male baby's groin from the testicles and the penis by allowing the testicles and the penis to extend through the hole (2) in the main cloth (1). Further, the penis is separated from the testicles by allowing the penis to extend through the second hole (4).

INDUSTRIAL APPLICABILITY

Thus, when a male baby wears the present invention, a drying condition is always maintained due to good ventilation and absorption provided by the present invention in isolating the groin, the testicles, and the penis through the use of absorbent and soft cloth.

Therefore, a male baby always feels pleasant and comfortable, when wearing the present invention and is also protected from many kinds of skin disease.

As shown in FIG. 1, the cloth 1 of the invention is elongated and rectangular and in use wraps under the child's groin as shown in FIG. 2 with a portion at the front and a portion at the rear. The cloth is covered by a diaper 5. The front portion of the cloth contains the U-shaped cutting line with the bottom of the U facing the portion of the rectangular cloth meant to cover the rear of the child. The hole 2 is formed only by the U-shaped cutting line. The hole 4 is within the U-shaped cutting line.

I claim:

1. A hygienic device for a male infant having a groin, a penis and a scrotum, the device comprising:
a soft, elongated rectangular, absorbent cloth for engaging the groin and having a front portion and a rear portion for covering a front and rear of the groin in use; a U-shaped cutting line in the front portion with a base of the line facing the rear portion, the cutting line alone forming a flap in the front portion which is movable to form a first hole in the front portion; the first hole being large enough for insertion of the scrotum therethrough in use; the flap having a second hole therethrough, the second hole being smaller than the first hole and being large enough for insertion of the penis therethrough in use; and a diaper over the cloth to cover the cloth in use.

* * * * *